United States Patent

Weferling et al.

[11] Patent Number: 5,973,194
[45] Date of Patent: Oct. 26, 1999

[54] PROCESS FOR PREPARING DIALKYLPHOSPHINATE SALTS

[75] Inventors: Norbert Weferling, Hürth; Hans-Peter Schmitz, Brühl; Günter Kolbe, Kerpen, all of Germany

[73] Assignee: Clariant GmbH, Frankfurt, Germany

[21] Appl. No.: 09/198,542

[22] Filed: Nov. 24, 1998

[30] Foreign Application Priority Data

Nov. 28, 1997 [DE] Germany ............................ 197 52 726
Nov. 10, 1998 [DE] Germany ............................ 198 51 768

[51] Int. Cl.⁶ ....................................................... C07F 9/30
[52] U.S. Cl. ................................ 562/8; 252/609; 524/133
[58] Field of Search ..................................................... 562/8

[56] References Cited

U.S. PATENT DOCUMENTS

| | | | |
|---|---|---|---|
| 3,914,345 | 10/1975 | Kleiner et al. . | |
| 4,036,811 | 7/1977 | Noetzel et al. . | |
| 4,590,014 | 5/1986 | Wolf et al. | 562/8 |
| 4,740,332 | 4/1988 | Thottathil | 562/8 |
| 5,780,534 | 7/1998 | Kleiner et al. | 524/133 |

FOREIGN PATENT DOCUMENTS 0699708  3/1996  European Pat. Off. .

*Primary Examiner*—Michael G. Ambrose
*Attorney, Agent, or Firm*—Susan S. Jackson

[57] ABSTRACT

The invention relates to a process for preparing dialkylphosphinate salts, which comprises a) reacting elemental yellow phosphorus with alkyl halides in the presence of alkali metal hydroxide or alkaline earth metal hydroxide to form a mixture which comprises as main constituents the salts of alkylphosphonous, phosphorous and hypophosphorous acids, b) adjusting the mixture to a pH below 7 and then reacting the mixture with olefins in the presence of a free-radical initiator and c) reacting the dialkylphosphinic acids obtained according to b) and/or alkali metal salts thereof with metal compounds of Mg, Ca, Al, Sb, Sn, Ge, Ti, Zn, Fe, Zr, Ce, Bi, Sr, Mn, Li, Na and/or K to give the metal dialkylphosphinate salts.

The invention likewise relates to the use of the metal dialkylphosphinate salts prepared by the process according to the invention to prepare flame retardants.

22 Claims, No Drawings

PROCESS FOR PREPARING DIALKYLPHOSPHINATE SALTS

The invention relates to a process for preparing dialkylphosphinate salts and their use.

Aluminum and calcium salts of dialkylphosphinic acids are known as flame retardants (EP 0 699 708 A1). They can be prepared by various processes.

DE 24 47 727 A1 describes low-flammability polyamide molding compositions which comprise a salt of a phosphinic acid or of a diphosphinic acid.

The abovementioned EP-A-0 699 708 A1 describes flame-retardant polyester molding compositions, the polyester molding compositions being flameproofed by adding calcium salts or aluminum salts of phosphinic or diphosphinic acids. These salts are obtained by reacting the corresponding dialkylphosphinic acids with calcium hydroxide or aluminum hydroxide.

The abovementioned processes have the disadvantage, in particular, that they start from starting compounds which cannot be prepared industrially, or only with great expense, therefore they are very highly uneconomic. This applies in particular to the particularly preferred dialkylphosphinic acids having short alkyl chains. Thus, for example, for preparing diethylphosphinic acid, no process which has been carried out or can be carried out industrially has to date been demonstrated.

Only DE 21 00 779 A1 describes a process for preparing alkyl dialkylphosphinates by the addition of olefins having from 2 to 22 carbon atoms to alkylphosphonous esters.

The object underlying the invention is to provide a process for preparing metal dialkylphosphinate salts which avoids the abovementioned disadvantages and starts from elemental phosphorus as feedstock. Furthermore, the synthesis is to succeed without complex purification steps and lead in a simple manner to the metal salts of dialkylphosphinic acids.

This object is achieved by a process of the type mentioned at the outset, which comprises a) reacting elemental yellow phosphorus with alkyl halides in the presence of alkali metal hydroxide or alkaline earth metal hydroxide to form a mixture which comprises as main constituents the salts of alkylphosphonous, phosphorous and hypophosphorous acids, b) adjusting the mixture to a pH below 7 and then reacting the mixture with olefins in the presence of a free-radical initiator and c) reacting the dialkylphosphinic acids obtained according to b) and/or alkali metal salts thereof with metal compounds of Mg, Ca, Al, Sb, Sn, Ge, Ti, Zn, Fe, Zr, Ce, Bi, Sr, Mn, Li, Na and/or K to give the metal dialkylphosphinate salts.

Preferably, in step a), the elemental yellow phosphorus is reacted with the alkyl halides in the presence of mixtures of aqueous alkali metal hydroxide and alkaline earth metal hydroxide.

Such a procedure has the advantage that it is easy to separate off phosphite formed in the reaction, for example as $Ca(HPO_3)$ Preferably, as alkyl halides, use is made of methyl chloride or methyl bromide.

Preferably, in step a), an organic solvent or a solvent mixture is present.

Preferably, in step a), the reaction is carried out in a 2-phase system in the presence of a phase-transfer catalyst.

The phase-transfer catalyst is preferably tetraalkylphosphonium halides, triphenylalkylphosphonium halides or tetraorganylammonium halides.

Preferably, in step b), the mixture is adjusted to a pH below 7 using mineral acids or carboxylic acids.

Preferably, as free-radical initiator, use is made of azo compounds.

Preferably, the azo compounds are cationic and/or non-cationic azo compounds.

Preferably, as cationic azo compounds, use is made of 2,2'-azobis(2-amidinopropane) dihydrochloride or 2,2'-azobis(N,N'-dimethyleneisobutyramidine) dihydrochloride.

Preferably, as non-cationic azo compounds, use is made of azobis(isobutyronitrile), 4,4'-azobis(4-cyano-pentanoic acid) or 2,2'-azobis(2-methylbutyronitrile).

Preferably, as free-radical initiator, use is made of inorganic peroxide and/or organic peroxide free-radical initiators.

Preferably, as inorganic peroxide free-radical initiators, use is made of hydrogen peroxide, ammonium peroxodisulfate and/or potassium peroxodisulfate.

Preferably, as organic peroxide free-radical initiators, use is made of dibenzoyl peroxide, di-tert-butyl peroxide and/or peracetic acid.

A broad selection of suitable free-radical initiators can be found, for example, in Houben-Weyl, Supplementary Volume 20, in the chapter "Polymerisation durch radikalische Initierung" [Polymerization by free-radical initiation] on pages 15–74.

Preferably, as olefins, use is made of unbranched or branched α-olefins.

Preferably, as olefins, use is made of ethylene, n-, i-propylene, n-, i-butene, n-, i-pentene, n-, i-hexene, n-, i-octene, 1-decene, 1,5-cyclooctadiene, 1,3-cyclopentadiene, dicyclopentadiene and/or 2,4,4-trimethylpentene isomeric mixture.

Equally preferably, as olefins, use is made of those having an internal double bond, cyclic olefins and cyclic or open-chain dienes and/or polyenes having from 4 to 20 carbon atoms.

Preferably, the olefins bear a functional group.

Suitable olefins are compounds of the formula

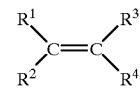

where $R^1$–$R^4$ can be identical or different and are hydrogen, an alkyl group having from 1 to 18 carbon atoms, phenyl, benzyl or alkyl-substituted aromatics.

Equally suitable are cycloolefins of the formula

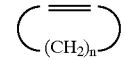

in particular cyclopentene, cyclohexene, cyclooctene and cyclodecene.

Use can also be made of open-chain dienes of the formula

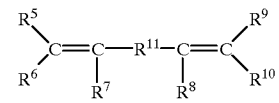

where $R^5$–$R^{10}$ are identical or different and are hydrogen or a $C_1$- to $C_6$-alkyl group and $R^{11}$ is $(CH_2)_n$ where n=0 to 6. Preference is given in this case to butadiene, isoprene and 1,5-hexadiene.

As cyclodienes, preference is given to 1,3-cyclopentadiene, dicyclopentadiene and 1,5-cyclooctadiene, and also norbornadiene.

Preferably, the metal compounds are metal oxides, metal hydroxides, metal hydroxide oxides, metal sulfates, metal acetates, metal nitrates, metal chlorides and/or metal alkoxides.

Particularly preferably, the metal compounds are aluminum hydroxide and aluminum sulfates.

Preferably, the dialkylphosphinic acids are reacted with the metal compounds at a temperature of from 20 to 150° C.

Preferably, the dialkylphosphinic acids are reacted with the metal compounds in an acetic acid and/or aqueous medium. This takes place, if necessary after adjusting to a pH range for the salt precipitation which is optimum for the respective dialkylphosphinic acid/metal compound system.

The invention also relates to the use of the metal dialkylphosphinate salts prepared by the process according to the invention to prepare flame retardants.

The invention also relates to the use of the metal dialkylphosphinate salts prepared by the process according to the invention to prepare flame retardants for thermoplastic polymers and thermosetting plastics.

The invention finally also relates to the use of the metal dialkylphosphinate salts prepared by the process according to the invention to prepare flame retardants for polystyrene, poly(ethylene terephthalate), poly-(butylene terephthalate) and polyamide.

The invention finally also relates to the use of the metal dialkylphosphinate salts prepared by the process according to the invention as additives in polymeric molding compounds.

The invention is described in more detail by the examples below.

EXAMPLE 1 a) Reaction of Yellow Phosphorus with Alkyl Halide 2 liters of toluene, in which 25 g (0.05 mol) of tributylhexadecylphosphonium bromide had been dissolved in advance, were placed in a 5 l stainless steel pressurized reactor and preheated to 60° C. 62 g (2 mol) of molten yellow phosphorus were introduced into the reactor cooled to 0° C. with vigorous stirring and then 202 g (4 mol) of methyl chloride were condensed in. Thereafter, 1000 g of a solution of 600 g of KOH in 400 g of water were introduced in the course of 1 hour, the temperature being maintained at 0° C. during this, and the mixture being reacted further for 1 hour at this temperature. The product mixture was warmed to room temperature, diluted with 400 ml of water and the reactor was then depressurized via a combustion system. Two homogeneous liquid phases were obtained, which were separated and analyzed.

The aqueous phase (mass: 1520 g) contained 64.2 mol % methylphosphonous acid, 15.8 mol % phosphorous acid and 14.2 mol % hypophosphorous acid and 2.8 mol % of dimethylphosphinic acid in the form of potassium salts thereof. The organic phase contained tributylhexadecylphosphonium bromide as main constituent.

b) Reaction of the Products from a) with Olefin

The aqueous phase obtained as described above was dissolved in 600 g of glacial acetic acid and concentrated on a rotary evaporator to about half of the original volume. The potassium acetate which precipitated out after cooling to room temperature was filtered off and washed with 100 g of cold glacial acetic acid. The glacial acetic acid solutions were combined and the resulting clear solution (1066 g) was transferred to a 2 l pressurized reactor and heated to 85° C. Ethylene was then forced in at 20 bar. In the course of 30 minutes, a solution of 10.8 g (0.04 mol) of 2,2'-azobis(2-amidinopropane) dihydrochloride in 50 ml of water was pumped in using a metering pump. The reaction temperature was maintained at from 85 to 90° C. for 4 hours. In the course of this, the ethylene pressure which had fallen was readjusted from time to time to 20 bar. The mixture was then cooled, depressurized and the product mixture was analyzed by $^{31}$P-NMR spectroscopy. The yield of product mixture was 1110 g.

Dialkylphosphinic acids: 79.8 molo %

Methylphosphonous acid: 0.8 mol %

Phosphorous acid: 14.9 mol %

Unidentified compounds: 4.5 mol % c) Preparation of the Dialkylphosphinate Salt

The reaction product obtained under b) was reacted with 58.5 g (0.75 mol) of aluminum hydroxide at 120° C. for 6 h in a 2 l pressurized reactor. The mixture was cooled to room temperature and the resulting suspension was filtered through a pressure filter. The filter residue was washed successively with 250 g of glacial acetic acid, 500 g of distilled water and 200 g of acetone. The colorless reaction product was dried at 140° C. for 8 h in an oil-pump vacuum. 228 g of colorless completely water-insoluble product having a bulk density of 230 g/l were obtained.

Analysis showed a P content of 26.3% and an Al content of 9.4%. For further analysis, a sample was dissolved in 25% strength aqueous NaOH and studied by $^{31}$P-NMR spectroscopy.

Dimethylphosphinic acid sodium salt: 2.6 mol %

Methylethylphosphinic acid sodium salt: 64.6 mol %

Diethylphosphinic acid sodium salt: 13.8 mol %

Methylphosphonous acid sodium salt: 0.1 mol %

Ethylphosphonous acid sodium salt: 0.3 mol %

Phosphorous acid sodium salt: 15.2 mol %

Unidentified compounds: 3.4 mol %

EXAMPLE 2 a) Reaction of Yellow Phosphorus with Alkyl Halide

A solution of 26.1 (0.05 mol) of tributylhexadecylphosphonium bromide in 1000 ml of toluene was introduced into a 5 l stainless steel pressure reactor and preheated to 60° C. After addition of 62 g (2 mol) of yellow phosphorus, the mixture was cooled to −10° C. with intensive stirring and then 202 g (4 mol) of methyl chloride were condensed in. Thereafter, 400 g of 50% strength aqueous sodium hydroxide solution were added in the course of 2 hours, the temperature being maintained at −10° C. 400 g of water were added in the course of one hour, thereafter the mixture was stirred for one more hour, heated to room temperature and then the reactor was depressurized via a combustion system. This produced two homogeneous liquid phases, which were separated and analyzed.

The aqueous phase (mass: 920 g) comprised 65.6 mol % methylphosphonous acid, 14.9 mol % phosphorous acid and 13.7 mol % hypophosphorous acid and 2.8 mol % dimethylphosphinic acid in the form of the sodium salts thereof.

b) Reaction of the Products from a) with Olefin 600 g of glacial acetic acid were added to the above solution. After distilling off the water present, the sodium acetate which had precipitated out was filtered off and washed with 100 g of glacial acetic acid. The glacial acetic acid solutions were combined and the resulting clear solution was transferred to a 2 l pressure reactor. After heating up the reaction mixture to 100° C., ethylene was introduced into the reactor up to saturation via a reducing valve set to 10 bar.

In the course of a period of 6 h, a solution of 6.6 g (0.04 mol) of azobis(isobutyronitrile) (AIBN) in 100 g of acetic acid was added uniformly under constant stirring at an ethylene pressure of 10 bar and a temperature of 100–105° C. After a post-reaction time of 1 h, depressurization of the reactor and cooling to room temperature, the contents were analyzed:

$^{31}$P NMR: dialkylphosphinic acids: 80.6 mol %
methylphosphonous acid: 0.8 mol %
phosphorous acid: 14.8 mol %
unidentified compounds: 3.8 mol %

The resulting reaction product was, as described in Example 1c), reacted with 58.5 g (0.75 mol) of aluminum hydroxide and worked up. This produced 230 g of colorless product. Analysis showed a P content of 25.8% and a Al content of 9.2%. For further analysis, a sample was dissolved in 25% strength aqueous NaOH and analyzed by $^{31}$P NMR spectroscopy:

Dimethylphosphinic acid sodium salt: 2.7 mol %
Methylethylphosphinic acid sodium salt: 66.0 mol %
Diethylphosphinic acid sodium salt: 13.5 mol %
Ethylphosphonous acid sodium salt: 0.1 mol %
Methylphosphonous acid sodium salt: 0.4 mol %
Phosphorous acid sodium salt: 13.8 mol %
Unidentified compounds: 3.5 mol %

EXAMPLE 3 a) Reaction of Yellow Phosphorus with Alkyl Halide

A solution of 29 g (0.05 mol) of tetraoctylphosphonium bromide in 1000 ml of toluene was introduced into a 5 l stainless steel pressure reactor and preheated to 60° C. After addition of 62 g (2 mol) of yellow phosphorus, the mixture was cooled to −10° C. with intensive stirring and then 202 g (4 mol) of methyl chloride were condensed in. Thereafter, the mixture was heated to 20° C. and 400 g of 50% strength aqueous sodium hydroxide solution were added in the course of 2 hours, the temperature being kept at 20° C. In the course of one hour, 400 g of water were added, thereafter the mixture was stirred for a further hour, heated to room temperature and then the reactor was depressurized via a combustion system. This produced two homogeneous liquid phases which were separated and analyzed.

The aqueous phase (mass: 940 g) comprised 51.2 mol % methylphosphonous acid, 24.7 mol % phosphorous acid and 18.5 mol % hypophosphorous acid and 2.6 mol % dimethylphosphinic acid in the form of the sodium salts thereof.

b) Reaction of the Products from a) with olefin 600 g of glacial acetic acid were added to the solution. After distilling off the water present, the sodium acetate which had precipitated out was filtered off and washed with 100 g of glacial acetic acid. The glacial acetic acid solutions were combined and the resulting clear solution was transferred to a 2 l pressure reactor. After heating up the reaction mixture to 100° C., ethylene was introduced into the reactor up to saturation by a reducing valve set to 5 bar. Over a period of 6 h, a solution of 9.7 g (0.04 mol) of dibenzoyl peroxide in 100 g of acetic acid were added uniformly with constant stirring at an ethylene pressure of 5 bar and a temperature of 100–105° C. After a post-reaction time of 1 h, depressurization of the reactor and cooling to room temperature, the contents were analyzed:

$^{31}$P-NMR: dialkylphosphinic acids: 68.8 mole %
methylphosphonous acid: 0.4 mole %
phosphorous acid: 26.1 mole %
unidentified compounds: 4.7 mole %

The resulting reaction product was, as described under 1c), reacted with 58.5 g (0.75 mol) of aluminum hydroxide and worked up. This produced 230 g of colorless product. Analysis showed a P content of 26.3% and an Al content of 9.4%. For further analysis, a sample was dissolved in 25% strength aqueous NaOH and analyzed by $^{31}$P-NMR spectroscopy:

Dimethylphosphinic acid sodium salt: 2.9 mol %
Methylethylphosphinic acid sodium salt: 51.1 mol %
Diethylphosphinic acid sodium salt: 17.0 mol %
Ethylphosphonous acid sodium salt: 0.2 mol %
Methylphosphonous acid sodium salt: 0.5 mol %
Phosphorous acid sodium salt: 24.9 mol %
Unidentified compounds: 3.4 mol %

We claim:

1. A process for preparing dialkylphosphinate salts, which comprises
   a) reacting elemental yellow phosphorus with alkyl halides in the presence of alkali metal hydroxide or alkaline earth metal hydroxide to form a mixture which comprises as main constituents the salts of alkylphosphonous, phosphorous and hypophosphorous acids,
   b) adjusting the mixture to a pH below 7 and then reacting the mixture with olefins in the presence of a free-radical initiator and
   c) reacting the dialkylphosphinic acids obtained according to b) and/or alkali metal salts thereof with metal compounds of Mg, Ca, Al, Sb, Sn, Ge, Ti, Zn, Fe, Zr, Ce, Bi, Sr, Mn, Li, Na and/or K to give the metal dialkylphosphinate salts.

2. The process as claimed in claim 1, wherein, in step a), the elemental yellow phosphorus is reacted with the alkyl halides in the presence of mixtures of aqueous alkali metal hydroxide and alkaline earth metal hydroxide.

3. The process as claimed in claim 1, wherein, as alkyl halides, use is made of methyl chloride or methyl bromide.

4. The process as claimed in claim 1, wherein, in step a), an organic solvent or a solvent mixture is present.

5. The process as claimed in claim 1, wherein, in step a), the reaction is carried out in a 2-phase system in the presence of a phase-transfer catalyst.

6. The process as claimed in claim 5, wherein the phase-transfer catalyst is tetraalkylphosphonium halides, triphenylalkylphosphonium halides or tetraorganylammonium halides.

7. The process as claimed in claim 1, wherein, in step b), the mixture is adjusted to a pH below 7 using mineral acids or carboxylic acids.

8. The process as claimed in claim 1, wherein, as free-radical initiator, use is made of azo compounds.

9. The process as claimed in claim 8, wherein the azo compounds are cationic and/or non-cationic azo compounds.

10. The process as claimed in claim 8, wherein, as cationic azo compounds, use is made of 2,2'-A azobis(2-amidinopropane) dihydrochloride or 2,2'-azobis(N,N'-dimethyleneisobutyramidine) dihydrochloride.

11. The process as claimed in claim 8, wherein, as non-cationic azo compounds, use is made of azobis (isobutyronitrile), 4,4'-azobis(4-cyanopentanoic acid) or 2,2'-azobis(2-methylbutyronitrile).

12. The process as claimed in claim 1, wherein, as free-radical initiator, use is made of inorganic peroxide and/or organic peroxide free-radical initiators.

13. The process as claimed in claim 12, wherein, as inorganic peroxide free-radical initiators, use is made of hydrogen peroxide, ammonium peroxodisulfate and/or potassium peroxodisulfate.

14. The process as claimed in claim 12, wherein, as organic peroxide free-radical initiators, use is made of dibenzoyl peroxide, di-tert-butyl peroxide and/or peracetic acid.

15. The process as claimed in claim 1, wherein, as olefins, use is made of unbranched or branched α-olefins.

16. The process as claimed in claim 1, wherein, as olefins, use is made of ethylene, n-, i-propylene, n-, i-butene, n-, i-pentene, n-, i-hexene, n-, i-octene, 1-decene, 1,5-cyclooctadiene, 1,3-cyclopentadiene, dicyclopentadiene and/or 2,4,4-trimethylpentene isomeric mixture.

17. The process as claimed in claim 1, wherein, as olefins, use is made of those having an internal double bond, cyclic olefins and cyclic or open-chain dienes and/or polyenes having from 4 to 20 carbon atoms.

18. The process as claimed in claim 1, wherein the olefins bear a functional group.

19. The process as claimed in claim 1, wherein the metal compounds are metal oxides, metal hydroxides, metal hydroxide oxides, metal sulfates, metal acetates, metal nitrates, metal chlorides and/or metal alkoxides.

20. The process as claimed in claim 1, wherein the metal compounds are aluminum oxide or aluminum sulfates.

21. The process as claimed in claim 1, wherein the dialkylphosphinic acids are reacted with the metal compounds at a temperature of from 20 to 150° C.

22. The process as claimed in claim 1, wherein the dialkylphosphinic acids are reacted with the metal compounds in an acetic acid and/or aqueous medium.

* * * * *